United States Patent [19]

Yamanouchi et al.

[11] Patent Number: 5,003,058

[45] Date of Patent: Mar. 26, 1991

[54] DNA CODING FOR ANTIGEN PROTEIN OF RINDERPEST VIRUS

[75] Inventors: Kazuya Yamanouchi, Fuchu; Yasuhiro Yoshikawa, Hoya; Masanobu Sugimoto, Shiki, all of Japan

[73] Assignee: Toa Nenryo Kogyo Kabushiki Kaisha, Tokyo, Japan

[21] Appl. No.: 90,550

[22] Filed: Aug. 28, 1987

[30] Foreign Application Priority Data

Aug. 29, 1986 [JP] Japan .................................. 61-201765
Mar. 26, 1987 [JP] Japan .................................. 62-70413

[51] Int. Cl.$^5$ ...................... C07H 21/04; C12N 15/45; C12N 21/02; A61K 39/155
[52] U.S. Cl. .................................... 536/27; 435/69.3; 435/172.3; 935/12; 514/12; 424/89
[58] Field of Search ................... 435/172.3, 235, 240.1; 536/27

[56] References Cited

PUBLICATIONS

Sato et al., Jpn J Med. Sci Biol. 34(6), 355–64.
Russel et al, "DNA Cloning of the Messenger RNS's . . . ", Chem. Abtracts, vol. 102, No. 19, pp. 160, 161472v., 6/13/85.
C. Gearld et al, "Measles Virus . . . ", Chem. Abstracts, vol. 106, No. 13, Abstract No. 97047p., 3/30/87.
Tsukiyama et al., "Molecular Cloning . . . ", Biological Abstract No. 107714, 1987.
F. Kobune et al., Archives of Virology 68, 271–277, 1981.
S. E. H. Russell et al., J. Gen. Virol. 66, 433–441, 1985.
H. Ishii et al., J. Gen. Virol. 67, 275–280, 1986.

*Primary Examiner*—Richard A. Schwartz
*Assistant Examiner*—M. Mosher
*Attorney, Agent, or Firm*—Wegner, Cantor, Mueller & Player

[57] ABSTRACT

A DNA coding for an entire or a part of an antigen protein of the rinderpest virus; a protein for the production of the DNA comprising the steps of preparing an mRNA from the rinderpest virus, preparing a cDNA library from the mRNA, selecting a cDNA coding for the target protein from the cDNA library, and cloning the selected cDNA in a cloning vector; and a protein for the production of the antigen protein of the rinderpest virus comprising the steps of transfecting a vector containing the DNA coding for the target protein into animal cells, culturing the animal cells to produce the antigen protein, and recovering the target protein from the cell culture.

4 Claims, 11 Drawing Sheets

Fig. 3-1

```
                                                                              Start
       20                      40                      60                      80
AGGATGCAAG ATCATCCACC ATGTCCTCCC CAAGAGACAG GGTCAATGCC TTCTACAAAG ACAACCTCCA ATTTAAGAAC XhoI          100                     120                     140                     160
ACTCGAGTGG TTCTTAATAA AGAGCAGCTC CTGATAGAAA GGCCTTACAT GTTGCTGGCG GTGCTGTTTG TTATGTTCCT 180                     200                     220                     240
GAGCCTAGTG GGGCTGTTGG CCATTGCAGG TATCAGACTC CACCGAGCTG CTGTCAACAC AGCAGAGATC AACAGTGGTC 260                     280                     300                     320
TGACGACAAG CATTGATATT ACCAAGTCTA TTGAGTACCA GGTCAAGGAC GTCTTAACTC CCCTCTTCAA AATAATTGGA Bg1II    360                     380                     400
      340                     TTCACAGATC TGACTAAATT CATATATCAGAC AAGATTAAGT TCCTTAACCC
GATGAGGTCG GGCTGAGGAC ACCTCAGAGA 420                     440                     460                     480
TGATAAAGAG TACGACTTCA GGGATATTAA AGTCCCCCAG AGAGAATCAA GATTAATTAT GATCAGTATT PvuII   500                     520                     540                     560
GTGCTCACAC AGCTGCTGAG GAGCTGATAA CTATGCTGGT CAATTCGTCT CTGGCAGGTA CTTCGGTACT ACCGACATCA
```

Fig. 3-2

```
                580              600              620              640
TTAGTCAACT TGGGGAGGAG CTGTACCGGG TCCACAACGA CTAAAGGTCA ATTCTCTAAC ATGTCATTGG CTCTTTCAGG 660              680              700              720
GATATACTCA GGTCGTGGCT ACAATATTTC ATCCATGATA ACAATCACTG AGAAAGGCAT GTACGGAAGC ACTTATCTAG 740              760              780              800
TCGGGAAACA TAATCAGGGA GCCAGGAGGC CAAGCACTGC TTGGCAACGG GATTACCCGAG TCTTTGAAGT AGGCATAATT

820            SacI 860                          BglII 880
AGAGAACTAG GACTGGGCAC ACCAGTGTTT CATATGACAA ACTACCTGGA GCTCCCAAGA CAGCCCGGAAT TGGAGATCTG

SphI           900              920              940              960
CATGCTAGCT CTAGGAGAGT TCAAATTAGC TGCCCTCTGC TTAGCTGATA ACTCTGTCGC ACTGCATTAC GGGGGGTTAA 980             1000             1020             1040
GGGACGACCA CAAGATCAGG TTTGTCAAAC TGGGAGTATG GCCATCACCA GCCGACTCAG ACACCCTGGC CACTCTTTCA 1060             1080           1100 PstI         1120
GCAGTAGATC CGACCTTGGA TGGGCTCTAT ATCACAACTC ATAGGGGAAT CATAGCTGCA GGGAAGGCCG TATGGGGTCGT
```

Fig. 3-3

```
          1140                    1160                    1180                    1200
CCCTGTGACG AGAACAGATG ACCAAAGGAA AATGGGACAG TGCCGCCGAG AGGCTTGTCG AGAGAAACCA CCACCTTTCT 1220                    1240                    1260                    1280
GTAACAGTAC AGATTGGGAG CCATTAGAGG CCGGCCGTAT ACCGGCATAT GGAATACTAA CTATCAGGCT GGGGCTGGCT 1300                    1320                    1340                    1360
GATAAGCTGA AATTGACCAT AATTTCAGAA TTTGGTCCCT TGATCACACA TGACTCAGGG ATGGACTTAT ACACCCCACT 1380                    1400                    1420                    1440
TGACGGTAAT GAGTACTGGC TGACTATTCC TCCATTGCAG AATTCAGCTT TAGGAACGGT GAACACCCTA GTTTTAGAGC 1460                    1480                    1500                    1520
CCAGTCTCAA AATTAGTCCT AACATCCTTA CTCTCCCCAT CAGGTCGGGG GGAGGTGACT GTTACACTCC CACTTACCTG

1540        SacI 1560                    1580                    1600
TCAGACCTGG CCGATGATGA TGTTAAACTG AGCTCCAATC TTGTAATCCT CCCGAGTAGA AACCTCCAAT ATGTGTCAGC

XbaI 1620                    1640                    1660                    1680
AACCTACGAC ACCTCTAGAG TTGAGCATGC CATTGTATAC TATATCTATA GCGCCGGGCG ACTATCATCG TATTACTACC
```

Fig. 3-4

```
                    1700              1720 PstI                              1740
CTGTTAAGTT GCCCATAAAG GGAGATCCTG TCAGCCTGCA GATAGGATGC TTCCCCTTGGG GCCTCAAGCT ATGGTGCCAT
                                                                                      1760
                    1780                             1800              1820
CATTTCTGCT CTGTTATAGA TTCAGGAACT CGCAAGCAGG TCACCCATAC AGGGGCAGTA GGGATTGAGA TCACTTGCAA
                                                                                      1840
  Stop           1860              BglII 1880                     PvuII 1900
TAGCAGATAG CAGTGTCTTG GCCCTACAAG ATCTTCGGAGA CCGGGACCCC CAACAGCTGT GGGACCAGGC ACCGCGCTGC
                                                                                      1920
                    1940
ACCATGCAGA CAGCTTTCAA TATTACCATT ATA(n)
```

Fig. 4-1

```
                    20                    40                    60                    80
AGGGCCAAAG AATCACATCG ACCCAAGCCG CCAGAAAGGA CAACACCATC GCCACCCAAC CAAACTGGAA ACCAGGGAGC
                   100                   120                   140                   160
AGCCACCCGC AGGGCCCAAA GCCCGGGCCC ACCCCACGAG CAGGGCGGAA CCAAGGGGCA GGCCCGCCCC ATGCACAGCA
                   180                   200                   220                   240
ACAGAACACC CCCAGATCCC CCACCAAAAG CCCCCCCGAC ACCGGGCAGA ACCCGAGGGC ACCCAGGAGA ATCCCCCGAC
                   260                   280                   300                   320
CCCAGACCCC CAACAGCAGC ATCCCCCACC CACCCCCCCC GTTCACTCCT CCCGGAACTT CCACTCCCAC CCCCTCCCGA
                   340                   360                   380                   400
GGAACAGAGG GCCCCATCCC CCCACTCCTC CCCGCCCCGG TCTCCAGCCC GAGACAACCC CCACACCCCA ACACGGAAGG
                   420                   440                   460                   480
TCTCGGTCGC TCAGGCCCGC CGAAGATCCA GCCAGAAAGA GCACCAAAGG CAGACCACCG GGCCCTGTGG TGGACCCCGC
                   500                   520                   540                   560
CAACCGGGAG CCCCAGACCC CCAAATCCAT CGGGCATCA AATCACGGCA GAGCAACCAA GGCACTGCTC AACAAACATG
```

Fig. 4-2

```
                580                600     →Start   620                 640
CCCAGACCAC CTACAAAGGA CCTAGCATGG GGATCTTATT TGCTGCCCTG CTAGCAATGA CTAACCCACA CTTAGCTACT 660                680                700                 720
GGCCAGATCC ACTGGGGCAA CCTTTCAAAA ATTGGAGTCG TAGGGACAGG TAGTGCCAGT TATAAGGTGA TGACCCAATC 740                760                780                 800
GAGTCACCAG TCACTAGTTA TAAAGCTGAT GCCCAATATC ACTGCTATAG ACAATTGCAC CAAAACAGAG ATTATGGAGT 820                840                860                 880
ACAAGAGGCT GTTGGGGACA GTGCTTAAGC CTATCAGGGA AGCTCTTAAC GCTATTACTA AGAACATAAA ACCAATCCAG 900                920                940                 960
AGTTCCACTA CCAGTAGGAG ACACAAGAGG TTCGCGGGAG TCGTTTTGGC TGGAGCCGCT CTCGGGGTTG CAACCGGAGC 980                1000               1020                1040
CCAGATTACA GCAGGGATTG CTCTTCATCA GTCAATGATG AATTCCCAAG CTATCGAAAG TCTTAAGGCA AGTCTGAAA 1060               1080               1100                1120
CAACCAATCA AGCAATTGAG GAAATACGAC AAGCGGGTCA AGAAATGGTC CTAGCGGTTC AGGGTGTCCA AGATTACATC
```

Fig. 4-3

```
                              1140                    1160                    1180                    1200
AACAATGAAC TGGTGCCTGC GATGGGCCAG CTATCGTGTG AAATTGTGGG TCAAAAGCTA GGGCTGAAAC TGCTTAGATA 1220                    1240                    1260                    1280
TTACACTGAA ATCTTGTCAT TATTTGGACC CAGCCTCAGG GACCCGGTCT CGGCTGAGCT TTCTATTCAG GCCTTAAGTT 1300                    1320                    1340                    1360
ACGCCCTTGGG TGGGACATT AATAAAAATAC TAGAAAAGCT TGGGTATAGC GGGAGTGATC TCCTTGCTAT ACTGGAAAGT 1380                    1400                    1420                    1440
AAGGGTATCA AGGCTAAGAT AACCTATGTG GATATCGAAA GTTACTTCAT TGTGCTCAGC ATAGCTTATC CGTCACTCTC 1460                    1480                    1500                    1520
CGAAATTAAG GGGGTGATAG TGCACCGTCT GGAGAGTGTC TCTTACAATA TAGGATCGCA GGAGTGGTAC ACCACAGTAC 1540                    1560                    1580                    1600
CGCGGGTATGT GGCAACCCAG GGTTACCTCA TTTCAAATTT CGATGACACA CCCTGTGCAT TCACTCCGGA GGGCACTATC 1620                    1640                    1660                    1680
TGCAGTCAAA ATGCAATATA CCCGATGAGC CCATTGCTCC AAGAATGTTT CCGTGGGTCA ACCAGGTCAT GTGCCCGTAC
```

Fig. 4-4

```
                      1700                   1720                   1740
ACTGGTTTTG GGGTCCATAG GGAATAGGTT TATACTATCT AAGGGGAACC TCATTGGCAA CTGTGCCTCT ATTTTGTGCA
                                                                                    1760

1780                   1800                   1820
AGTGCTACAC CACTGGCTCA ATAATAAGTC AAGACCCTGA CAAGATCCTA ACATATATAG CTGCAGACCA ATGCCCCGTC
                                                                                    1840

1860                   1880                   1900
GTAGAAGTAG GCGGTGTAAC CATCCAGGTC GGGAGCAGGG AGTACTCCGA TGCAGTGTAC CTGCATGAAA TAGATCTTGG
                                                                                    1920

1940                   1960                   1980
CCCACCAATA TCGCTAGAGA AGCTGGATGT GGGGACTAAC CTCTGGAATG CAGTGACAAA ATTGGAGAAA GCCAAGGATC
                                                                                    2000

2020                   2040                   2060
TACTAGATTC ATCTGATCTG ATCCTGGAAA ACATCAAGGG TGTTTCAGTC ACGAACACAG GTTACATTCT AGTCGGAGTC
                                                                                    2080

2100                   2120                   2140
GGGTTGATTG CAGTGGTGGG GATCCCTCATT ATTACCTGTT GTTGTAAGAA GCGCAGGACT GACAACAAAG TCTCCACTAT
                                                                                    2160

2180                   2200           Stop  2220
GGTCTTGAAC CCGGGTCTTA GACCAGATCT TACTGGTACA TCTAAATCCT ACGTACGGTC GTTGTAGCAG GTGTGTCTCC
                                                                                    2240
```

Fig. 4-5

```
                           2260                                   2280                                   2300                                  2320
       CATGTGATCA ATGTCCCCGA ATACCTTATC AAACCTTACA ATGCTTTGTC CTCCTCGCAG CCAGCTAGTC GCTATCCTCA
                    2340
       GCAGGCACCA TGCTCGATCG CTCATTAATT GCTACAAAG
```

DNA CODING FOR ANTIGEN PROTEIN OF RINDERPEST VIRUS

BACKGROUND OF THE INVENTION

1. Field of the Invention

The present invention relates to DNA coding for antigen proteins of the rinderpest virus, a process for the production of that DNA, and a process for the production of the antigen protein using that DNA.

2. Description of the Related Art

Rinderpest is often prevalent in many areas of the world, such as the Middle and Near East, and Africa etc., and therefore, there is intensive research into the development of vaccines for the rinderpest virus.

In the development of vaccines through genetic engineering, processes wherein a gene coding for an antigen protein of the vaccine is expressed in *E. coli*, yeast or animal cells to obtain the antigen protein, and processes wherein a gene coding for an antigen protein is integrated into a vaccinea virus to construct a recombinant virus for the production of a live vaccine are known. To carry out such processes, a gene coding for an antigen protein of the rinderpest virus must be cloned.

A rinderpest virus strain L that can be grown in Vero cells has been constructed (F. Kobune et al., *Archives of Virology*, 68, 271–277, 1981). Also, a rinderpest virus strain L (L 13) that can be grown in Vero cells has been developed (*J. Gen. Virol.* 67, 271, 1986).

The cloning of a cDNA coding for an F protein of the canine distemper virus has been disclosed by S. E. H. Russell, *J. Gen. Virol.* 66, 435–441, 1985.

Nevertheless, a gene coding for an antigen protein of the rinderpest virus has not yet been cloned.

SUMMARY OF THE INVENTION

Accordingly, the present invention provides a cloned genes coding for antigen proteins of the rinder-pest virus and a process for the production of that gene, and a process for the production of an antigen protein which is promising as an active ingredient for vaccines against the rinderpest virus.

More particularly, the present invention provides a DNA coding for an entire or a part of an antigen protein of the rinderpest virus.

The present invention also provides a process for the production of the above-mentioned DNA comprising the steps of:

preparing an mRNA from the rinderpest virus;
preparing a cDNA library from the mRNA;
selecting a cDNA coding for the target protein from the cDNA library; and
cloning the selected cDNA in a cloning vector.

The present invention also provides a process for the production of the above-mentioned protein comprising the steps of:

transfecting a vector containing the DNA coding for the target protein into animal cells;
culturing the animal cells to produce the antigen protein; and
recovering the target protein from the cell culture.

BRIEF DESCRIPTION OF THE DRAWINGS

FIGS. 4–1 to 4–5 represent a nucleotide sequence containing a fusion protein gene of the rinderpest virus, wherein, in the sequence, ATG at the 587th to 589th position is a translation start codon and TAG at the 2225th to 2227th position is a translation stop codon, and a reading frame flanked by these codons (represented by a thick line in FIG. 2, RV-F-2) shows the codes for a fusion protein.

DESCRIPTION OF THE PREFERRED EMBODIMENT

A. Cloning of genes

Figure 1:
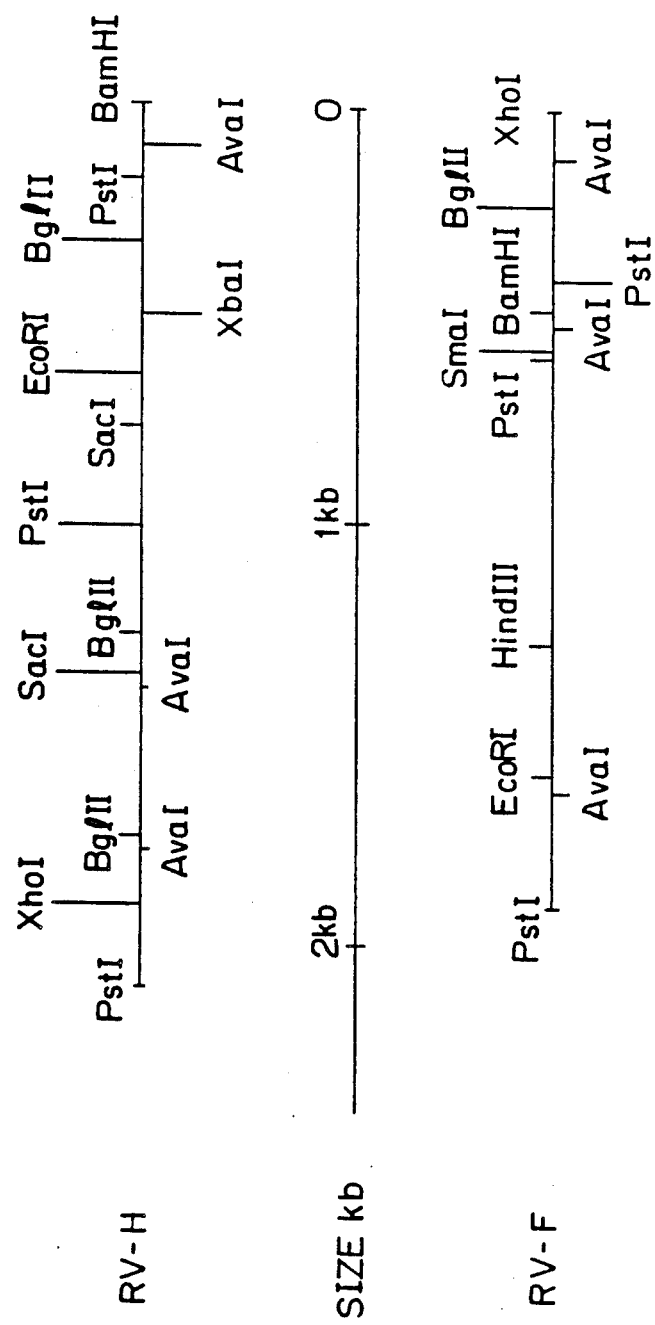
FIG. 1 represents a restriction enzyme cleavage map of a cDNA insert RV-H in a plasmid pDH-RVH and a restriction enzyme cleavage map of a cDNA insert RV-F in a plasmid pDH-RVF.

Since it is believed that the proteins effective as antigens to the rinderpest virus are the hemagglutinin protein (H protein) and the fusion protein (F protein), according to the present invention, the genes coding for these proteins were cloned.

(1) Extraction of mRNA

The rinderpest virus L strain that can be grown in Vero cells (rinderpest virus L 13 strain) was cultured, mRNA was extracted from the culture, and the cDNA was prepared from the mRNA according to the Okayama-Berg method (Okayama and Berg, *Mol. Cell Boil.*, 2, 161–170, 1983; and *Mol. Cell Biol.*, 3, 280–289, 1983).

More specifically, the rinderpest virus L 13 was used as an origin of the mRNA. The L 13 strain was obtained by fusing a rabbit lymphocyte infected with a rabbit-adapted passaged strain of the rinderpest virus (L-lapinized strain and F-Vero cells) under polyethylene glycol, and passaging 15 generations. Sub-confluent F-Vero cells in eight Petri dishes each having a diameter of 6 cm were inoculated with the L 13 strain at an m.o.i. of 1. The culture was passaged on teh next day, and 24 hours after the passage, 20 μg/ml of actinonycin D was added to the culture to inhibit a synthesis of cellular mRNA and incubation was continued for an additional 5 hours. The recovered cells were centrifuged in 6 M of guanidium isothiocyanate (GTC), 5 mM of sodium citrate and 0.5% of Sarkosyl - 5.7 M of CsCl and 0.1 M of EDTA at 35,000 rpm (150,000 XG) for more than 12 hours, according to the guanidinum-cesium chloride method, to recover the RNA (T. Maniatis et al., *Molecular Cloning*, p 196, 1982).

The thus-recovered RNA was then applied to an oligo (dT) cellulose column, and the adsorbed RNA was eluted by 10 mM Trsi-HCl (pH 7.5) buffer containing 1 mM EDTA and 0.05% SDS to obtain a poly A$^{(+)}$ RNA according to a known procedure (T. Maniatis et al., *Molecular Cloning*, p 197, 1982).

(2) Preparation of probes

According to the present invention, to confirm the presence of a target mRNA in the above-prepared poly $A^{(+)}$ RNA, and to screen cDNA library as described hereinafter in detail, an H gene of a subacute sclerosing panencephalitis (SSPE) virus was used as a probe (designated as H gene probe or SSPE-H-cDNA probe) to detect and screen the gene coding for the H protein (H gene) of the rinderpest virus; and the F gene of the canine distemper virus (CDV) was used as a probe (designated as F gene probe or CDV-F-cDNA probe) to detect and screen the gene coding for an F protein (F gene) of the rinderpest virus These genes were selected as probes because the above-mentioned SSPE virus and CDV, as well as the rinderpest virus, belong to the common genus Morbillivirus and these riruses are closely related to each other, and therefore, it is considered that the nucleotide sequences thereof will have a high homology.

The above-mentioned probes were prepared by obtaining an SSPE virus DNA and CDV DNA and labeling these DNA with a radioisotope $^{35}S$ (T. Maniatis et al., *Molecular Cloning,* p 109, 1982).

More specifically, a cDNA library was made from SSPE infected cells, and SSPE H cDNA was selected by the use of measles virus H probe (Billeter et al. 1984, Virology 145 195). (DV H DNA was made according to Russel et al. (1985) (J. Gen. Virol, 66 433.). Each DNA thus-prepared was incubated with three unlabeled deoxyribonucleotides dATP, dGTP and dTTP, and a $^{35}S$-labeled deoxyribonucleotide $^{35}S$-dCTP-$\gamma$S in the presence of *E. coli* DNA polymerase I in a Tris-HCl (pH 7.8) buffer. The labeled DNA was then separated from unreacted $^{35}S$-dCTP-YS by a Sephadex G25 column.

(3) Detection of H protein mRNA and F protein mRNA in poly $A^{(+)}$ RNA

The poly RNA prepared as described above was denatured with glyoxal or formamide, and separated by Agarose gel electrophoresis, and the separated mRNAs were subjected to hybridization with the above-mentioned SSPE-H-cDNA probe or CDV-F-cDNA probe according to the conventional Northern hybridization method. As a result, a 1.96 kb mRNA which hybridizes with the SSPE-H-cDNA probe and a 2.2 kb mRNA which hybridizes with the COV-F-cDNA were detected. This result suggests that the poly $A^{(+)}$ RNA preparation includes an mRNA coding for the H protein of the rinder-pest virus and an mRNA coding for the F protein of the rinderpest virus.

(4) Preparation of cDNA library

A cDNA library was prepared from the above-mentioned poly $A^{(+)}$ RNA preparation according to the Okayama-Berg method (Okayama H. and P. Berg, *Mol. Cell Biol.,* 2, 161, 1982; and Mol. Cell Biol., 3, 280, 1983). As a vector, an oligo dT-tailed (T=17) plasmid primer (pcDV-1) and an oligo dG-tailed (G=12) pL-1 Hind III linker were used.

More specificially, 8 $\mu$g of the above-mentioned poly $A^{(+)}$ RNA, 2 $\mu$g of the dT-tailed plasmid primer (pcDV-1), 2 mM of four dNTPs including $^{35}S$-dCTP, and 20.6 units of a reverse transcriptase (RTase) were incubated in 40 $\mu$l of a reaction mixture containing 100 mM of Tris-Hcl (pH 8.3), 10 mM of $MgCl_2$, 140 mM of KCl, 2 mM of methylmercury hydroxide, 20 mM of mercaptoethanol, and 1 mM of RNase inhibitor at 42° C. for 60 minutes, to form a cDNA-plasmid To the reaction mixture, 3.5 mM of dCTP and 30 units of terminal transferase were added, resulting in the formation of 73.5 $\mu$l total volume of the reaction mixture The reaction mixture was subjected to reaction at 37° C. for 3 minutes, and 2.5 mM of EDTA containing 0.5% (final concentration) of SDS was added to the reaction mixture to terminate the reaction The reaction mixture was extracted with chloroform and phenol, and the DNA was then precipitated with ethanol.

The thus-prepared cDNA-plasmid was digested with 20 units of Hind III in 40 $\mu$l of a buffer containing 10 mM of Tris-HCl (pH 7.5), 50 mM of NaCl, 10 mM of MgCl and 1 mM of dithiothreitol, at 37° C for 2 hours. Then, 120 mg of the digested cDNA-plasmid and 35 $\mu$g of the PL-1 linker were incubated in 40 $\mu$l of a reaction mixture containing 0.1 M NaCl, 10 mM Tris-HCl (pH 7.8) and 1 mM EDTA, first at 65° C. for 5 minutes and that of 42° C. for 60 minutes, and the reaction mixture was then cooled to a room temperature to allow annealing. After the reaction mixture was cooled to 0° C., 0.3 $\mu$g of *E. coli* DNA ligase was then added to the reaction mixture, and the reaction mixture was incubated at 12° C. overnight.

Then, 200 mg of *E. coli* DNA ligase, 0.450 units of RNase H and 0.8 units of DNA polymerase were added to the reaction mixture to make the total volume of the mixture of 48 $\mu$l, and the temperature of the reaction mixture was then increased stepwise to 12° C., 15° C., 20° C., and to 25° C., for 30 minutes at each temperature, resulting in digestion of an mRNA region, formation of a double-stranded cDNA and ligation of the resulting cDNA, to complete the construction of plasmids containing the cDNA.

The thus-obtained plasmids were used to transform *Escherichia coli* DH-5 and *E. coli* MC1061, and a cDNA library comprising 7,700 clones and a cDNA library comprising 7,300 clones (total 15,000 clones) were obtained from *E. coli* DN-5 and *E. coli* MC1061, respectively.

(5) Screening of cDNA library

From among the above-mentioned 15,000 clones, 109 clones were screened by the colony hybridization method. As a result, a clone hybridizing with the SSPE-H-cDNA probe and a clone hybridizing with CDV-F-cDNA were obtained These clones were designated as *Escherichia coli* DH-RVH and *Escherichia coli* DH-RVF respectively; and plasmids in these *E. coli* cells were designated as pDH-RVH and pDH-RVF. The size of cDNA insert (designated as RV-H) in the plasmid pDH-RVH was about 2.2 kb, and the size of the cDNA insert (designated as RV-F) in the plasmid pDH-RVF was about 1.6 kb. It was considered that these cDNA inserts contained approximately the entire coding regions for the H protein and F protein of the rinderpest virus, respectively The above-mentioned *Escherichia coli* DH-RVH was deposited with the Fermentation Research Institute Agency of Industrial Science and Technology (FRI), Higashi 1-1-3, Yatabe-cho, Tsukuba-gun, Ibaraki-ken, Japan, as FERM BP-1165 under the Budapest treaty on Aug. 29, 1986. The above-mentioned *Escherichia coli* DH-RVF was deposited with the FRI as FERM BP-1164 under the Budapest treaty on Aug. 29, 1986.

By repeating the same procedure as described above, a clone hybridizing with teh SSPE-H-cDNA probe and a clone hybridizing with the SSPE-H-cDNA were obtained. These clones were designated as *Escherichia coli* DH-RVH-2 and *Escherichia coli* DH-RVF-2, respectively; and plasmids in these E. coli cells were designated as pDH-RVH-2 and pDH-RVF-2, respectively. The size of the cDNA insert (designated as RV-H-2) in the plasmid pDH-RVH-2 was about 3.2 kb, and the size of the cDNA insert (designated as RV-F-2) in the plasmid pDH-RVF-2 was about 2.4 kb. The RV-H-2 contained an entire coding region for the H protein of the rinderpest virus, and the RV-F-2 is considered to contain an entire coding region for the F protein of the rinderpest virus.

The above-mentioned *Escherichia coli* DH-RVH-2 was deposited with the FRI as FERM BP-1319 under the Budapest treaty on Mar. 24, 1987. The above-mentioned Escherichia coli DH-RVF-2 was deposited with the FRI as FERM BP-1318 under the Budapest treaty on Mar. 24, 1987.

(6) Restriction enzyme cleavage map

Figure 2:
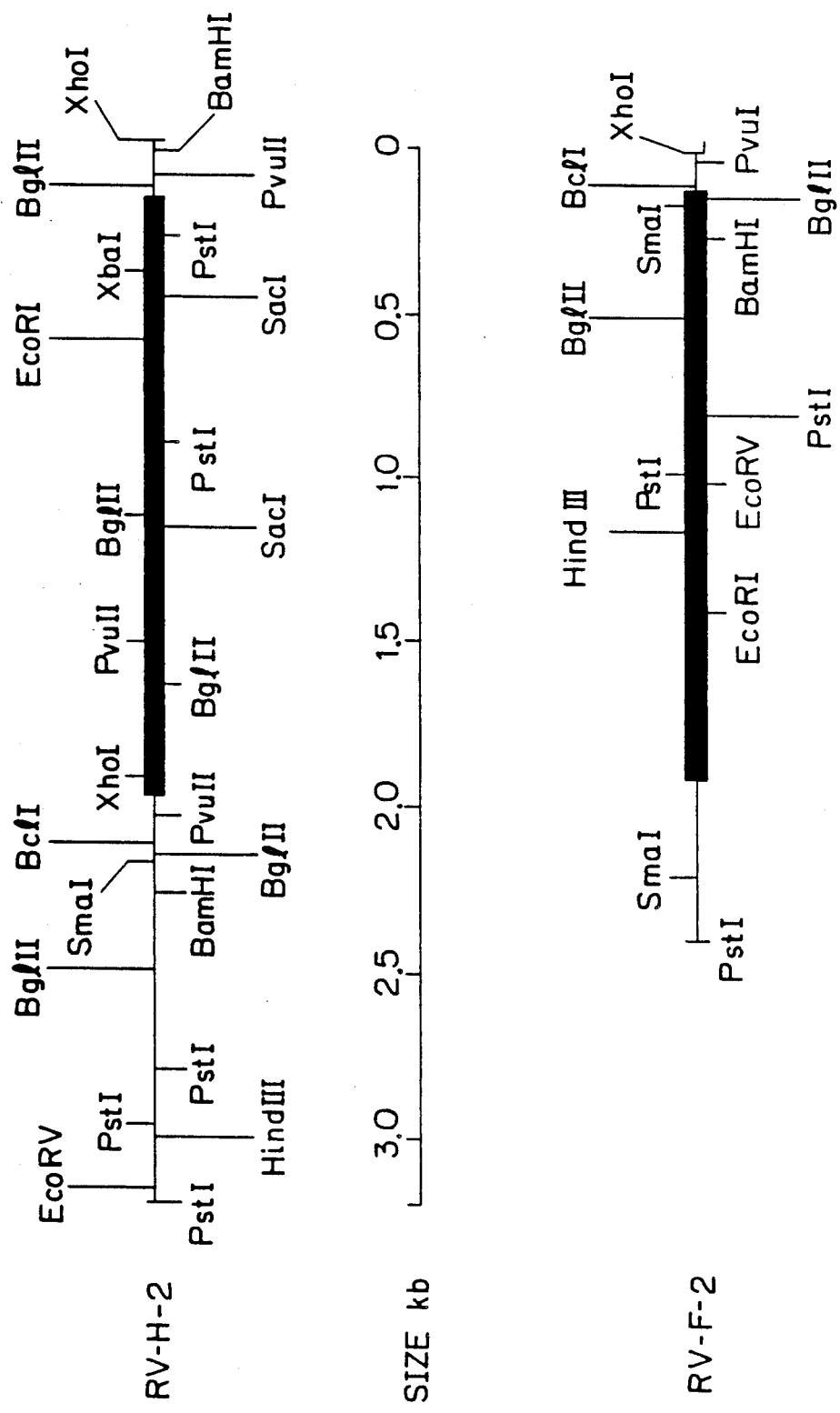
FIG. 2 represents a restriction enzyme cleavage map of a cDNA insert RV-H-2 in a plasmid pDH-RVH-2 and a restriction enzyme cleavage map of a cDNA insert RV-F-2 in a plasmid pDH-RVF-2, wherein the thick line in the RV-H-2 represents a portion corresponding to a nucleotide sequence coding for a hemagglutinin protein (H protein) of the rinderpest virus shown in FIG. 3; and, FIGS. 3–1 to 3–4 represent a nucleotide sequence containing a hemagglutinin gene of the rinderpest virus, wherein, in the sequence, ATG at the 21st to 23rd position is a translation start codon and TAG at the 1848th to 1850th position is a translation stop codon, and a reading frame flanked by these codons (represented by a thick line in FIG. 2, RV-H-2) shows the codes for a hemagglutinin protein.

The restriction enzyme cleavage sites of the above-mentioned cDNA inserts were analyzed to determine restriction enzyme cleavage maps, according to a conventional procedure. FIG. 1 represents the restriction enzyme cleavage maps for the cDNA inserts RV-H and RV-F, and FIG. 2 represents the restriction enzyme cleavage maps for the cDNA inserts RV-H-2 and RV-F-2.

(7) Determination of nucleotide sequences of cDNAs coding for H protein and F protein The plasmids pDH-RVH and pDH-RVH-2 were digested with restriction enzymes Bam HI, Pvu II, Pst I, Eco RI, Hind III, and Sma I, and DNA fragments of several hundred base pairs in length were separated. Each DNA fragment was inserted to a polylinker site of a phage M13 DNA, and the nucleotide sequence was determined according to the Sanger dideoxy chain termination method. The result is shown in FIGS. 3-1 to 3-4.

According to a similar procedure, nucleotide sequence coding for F protein was determined. The result is shown in FIGS. 4-1 to 4-5.

(8) Expression of gene

COS7 cells were cultured in a cell culture chamber in 1 ml of Eagle's minimum essential medium containing 10% felal calf serum at 37° C. for 24 hours. The DNA of the plasmid pDH-RVH-2was coprecipitated with calcium phosphate, and 1 µg of the precipitated DNA was transfected to the cultured COS7 cells. The cells were then treated with a DMEM medium containing 10% dimethyl sulfoxide and 5% fetal calfserum. Fresh medium was added to the cells, and culturing was carried out at 37° C. for two tothree days. The cells were then fixed withacetone, and were observed by an indirect fluorescent antibody technique using an antibody specific to the rubeola virus. In this technique, an antigen H reactive with the antibody was observed on the cells. In same manner, it was confirmed that the pDH-RVF and pDH-RVF2 expressed an antigen F.

The present cDNA coding for the hemagglutinin protein of the rinderpest virus, and the cDNA coding for the fusion protein of the rinderpest virus are useful as gene starting materials in a process for the construction of a recombinant virus by inserting them into, for example, a vaccinia virus, or in a process for the production of antigen proteins by expressing the cDNA in E. coli, yeast or animal cells.

Moreover, the present cDNA and fragments thereof are useful as hybridization probes for screening genes of different origin but containing a similar nucleotide sequence, such as cDNA of different origin. Moreover, the present cDNA and fragments thereof are useful as a component of a kit for the detection of the rinderpest virus and related viruses.

Note, the procedures disclosed in the present specification can be applied to the cloning of other cDNAs coding for an antigen protein or a part thereof of the rinderpest virus. Then cDNA are also covered by the present invention.

We claim:

1. A DNA coding for a hemagglutinin protein antigen of a rinderpest virus.

2. DNA according to claim 1, wherein the DNA has the following nucleotide sequence:

ATGTCCTCCC CAAGAGACAG GGTCAATGCC TTCTACAAAG ACAACCTCCA ATTTAAGAAC ACTCGAGTGG TTCTTAATAA AGAGCAGCTC CTGATAGAAA GGCCTTACAT GTTGCTGGCG GTGCTGTTTG TTATGTTCCT GAGCCTAGTG GGGCTGTTGG CCATTGCAGG TATCAGACTC CACCGAGCTG CTGTCAACAC AGCAGAGATC AACAGTGGTC TGACGACAAG CATTGATATT ACCAAGTCTA TTGAGTACCA GGTCAAGGAC GTCTTAACTC CCCTCTTCAA AATAATTGGA GATGAGGTCG GGCTGAGGAC ACCTCAGAGA TTCACAGATC TGACTAAATT CATATCAGAC AAGATTAAGT TCCTTAACCC TGATAAAGAG TACGACTTCA GGGATATTAA CTGGTGCATC AGTCCCCCAG AGAGAATCAA GATTAATTAT GATCAGTATT GTGCTCACAC AGCTGCTGAG GAGCTGATAA CTATGCTGGT CAATTCGTCT CTGGCAGGTA CTTCGGTACT ACCGACATCA TTAGTCAACT TGGGGAGGAG CTGTACCGGG TCCACAACGA CTAAAGGTCA ATTCTCTAAC ATGTCATTGG CTCTTTCAGG GATATACTCA GGTCGTGGCT ACAATATTTC ATCCATGATA ACAATCACTG AGAAAGGCAT GTACGGAAGC ACTTATCTAG TCGGGAAACA TAATCAGGGA GCCAGGAGGC CAAGCACTGC TTGGCAACGG GATTACCGAG TCTTTGAAGT AGGCATAATT AGAGAACTAG GACTGGGCAC ACCAGTGTTT CATATGACAA ACTACCTGGA GCTCCAAGA CAGCCGGAAT TGGAGATCTG CATGCTAGCT CTAGGAGAGT TCAAATTAGC TGCCCTCTGC TTAGCTGATA ACTCTGTCGC ACTGCATTAC GGGGGGTTAA GGGACGACCA AGATCAGG TTTGTCAAAC TGGGAGTATG GCCATCACCA GCCGACTCAG ACACCCTGGC CACTCTTTCA GCAGTAGATC CGACCTTGGA TGGGCTCTAT ATCACAACTC ATAGGGGAAT CATAGCTGCA GGGAAGGCCG TATGGGTCGT CCCTGTGACG AGAACAGATG ACCAAAGGAA AATGGGACAG TGCCGCCGAG AGGCTTGTCG AGA-

GAAACCA CCACCTTTCT GTAACAGTAC
AGATTGGGAG CCATTAGAGG
CCGGCCGTAT ACCGGCATAT GGAATAC-
TAA CTATCAGGCT GGGGCTGGCT GA-
TAAGCTGA AATTGACCAT AATTT-
CAGAA TTTGGTCCCT TGATCACACA
TGACTCAGGG ATGGACTTAT ACACC-
CCACT TGACGGTAAT GAGTACTGGC
TGACTATTCC TCCATTGCAG AATT-
CAGCTT TAGGAACGGT GAACACCCTA
GTTTTAGAGC CCAGTCTCAA AAT-
TAGTCCT AACATCCTTA CTCTCCCCAT
CAGGTCGGGG GGAGGTGACT GTTA-
CACTCC CACTTACCTG TCAGACCTGG
CCGATGATGA TGTTAAACTG AGCT-
CCAATC TTGTAATCCT CCCGAGTAGA
AACCTCCAAT ATGTGTCAGC AACCTAC-
GAC ACCTCTAGAG TTGAGCATGC
CATTGTATAC TATATCTATA
GCGCCGGGCG ACTATCATCG TATTAC-
TACC CTGTTAAGTT GCCCATAAAG
GGAGATCCTG TCAGCCTGCA GATAG-
GATGC TTCCCTTGGG GCCTCAAGCT
ATGGTGCCAT CATTTCTGCT
CTGTTATAGA TTCAGGAACT CGCAAG-
CAGG TCACCCATAC AGGGGCAGTA
GGGATTGAGA TCACTTGCAA TAG-
CAGATAG

3. A DNA coding for a fusion protein antigen of a rinderpest virus.

4. DNA according to claim 3, wherein the DNA has the following nucleotide sequence:

ATGG GGATCTTATT TGCTGCCCTG CTAG-
CAATGA CTAACCCACA CTTAGCTACT
GGCCAGATCC ACTGGGGCAA
CCTTTCAAAA ATTGGACTCG TAGG-
GACAGG TAGTGCCAGT TATAAGGTGA
TGACCCAATC GAGTCACCAG TCAC-
TAGTTA TAAAGCTGAT GCCCAATATC
ACTGCTATAG ACAATTGCAC CAAAACA-
GAG ATTATGGAGT ACAAGAGGCT
GTTGGGGACA GTGCTTAAGC CTAT-
CAGGGA AGCTCTTAAC GCTATTACTA
AGAACATAAA ACCAATCCAG AGTT-
CCACTA CCAGTAGGAG ACACAAGAGG
TTCGCGGGAG TCGTTTTGGC
TGGAGCCGCT CTCGGGGTTG CAACC-
GCAGC CCAGATTACA GCAGGGATTG
CTCTTCATCA GACAATGATG AATTC-
CCAAG CTATCGAAAG TCTTAAGGCA
AGTCTGGAAA CAACCAATCA AG-
CAATTGAG GAAATACGAC
AAGCGGGTCA AGAAATGGTC
CTAGCGGTTC AGGGTGTCCA AGAT-
TACATC AACAATGAAC TGGTGCCTGC
GATGGGCCAG CTATCGTGTG
AAATTGTGGG TCAAAAGCTA
GGGCTGAAAC TGCTTAGATA TTACACT-
GAA ATCTTGTCAT TATTTGGACC
CAGCCTCAGG GACCCGGTCT
CGGCTGAGCT TTCTATTCAG
GCCTTAAGTT ACGCCTTGGG
TGGGGACATT AATAAAATAC TA-
GAAAAGCT TGGGTATAGC CCCACT-
GATC TCCTTGCTAT ACTGGAAAGT
AAGGGTATCA AGGCTAAGAT AACC-
TATGTG GATATCCAAA GTTACTTCAT
TGTGCTCAGC ATAGCTTATC
CGTCACTCTC CGAAATTAAG
GGGGTGATAG TGCACCGTCT GGA-
GACTGTC TCTTACAATA TAGGATCGCA
GGAGTGGTAC ACCACAGTAC
CGCGGTATGT GGCAACCCAG
GGTTACCTCA TTTCAAATTT CGAT-
GACACA CCCTGTGCAT TCACTCCGGA
GGGCACTATC TGCAGTCAAA ATG-
CAATATA CCCGATGAGC CCATTGCTCC
AAGAATGTTT CCGTGGGTCA AC-
CAGGTCAT GTGCCCGTAC
ACTGGTTTTG GGGTCCATAG GGAA-
TAGGTT TATACTATCT AAGGGGAACC
TCATTGGCAA CTGTGCCTCT ATTTTGT-
GCA AGTGCTACAC CACTGGCTCA
ATAATAAGTC AAGACCCTGA CAA-
GATCCTA ACATATATAG CTGCAGACCA
ATGCCCCGTC GTAGAAGTAG
GCGGTGTAAC CATCCAGGTC GGGAG-
CAGGG AGTACTCCGA TGCAGTGTAC
CTGCATGAAA TAGATCTTGG CCCAC-
CAATA TCGCTAGAGA AGCTGGATGT
GGGGACTAAC CTCTGGAATG CAGT-
GACAAA ATTGGAGAAA GCCAAGGATC
TACTAGATTC ATCTGATCTG ATCCT-
GGAAA ACATCAAGGG TGTTTCAGTC
ACGAACACAG GTTACATTOT AGTC-
GGAGTC GGGTTGATTG CAGTGGTGGG
GATCCTCATT ATTACCTGTT
GTTGTAAGAA GCGCAGGACT GACAA-
CAAAG TCTCCACTAT GGTCTTGAAC
CCGGGTCTTA GACCAGATCT TACTG-
GTACA TCTAAATCCT ACGTACGGTC
GTTGTAG

\* \* \* \* \*